Jan. 24, 1950 E. S. BOERNER Plant Pat. 913
ROSE PLANT
Filed Dec. 2, 1948
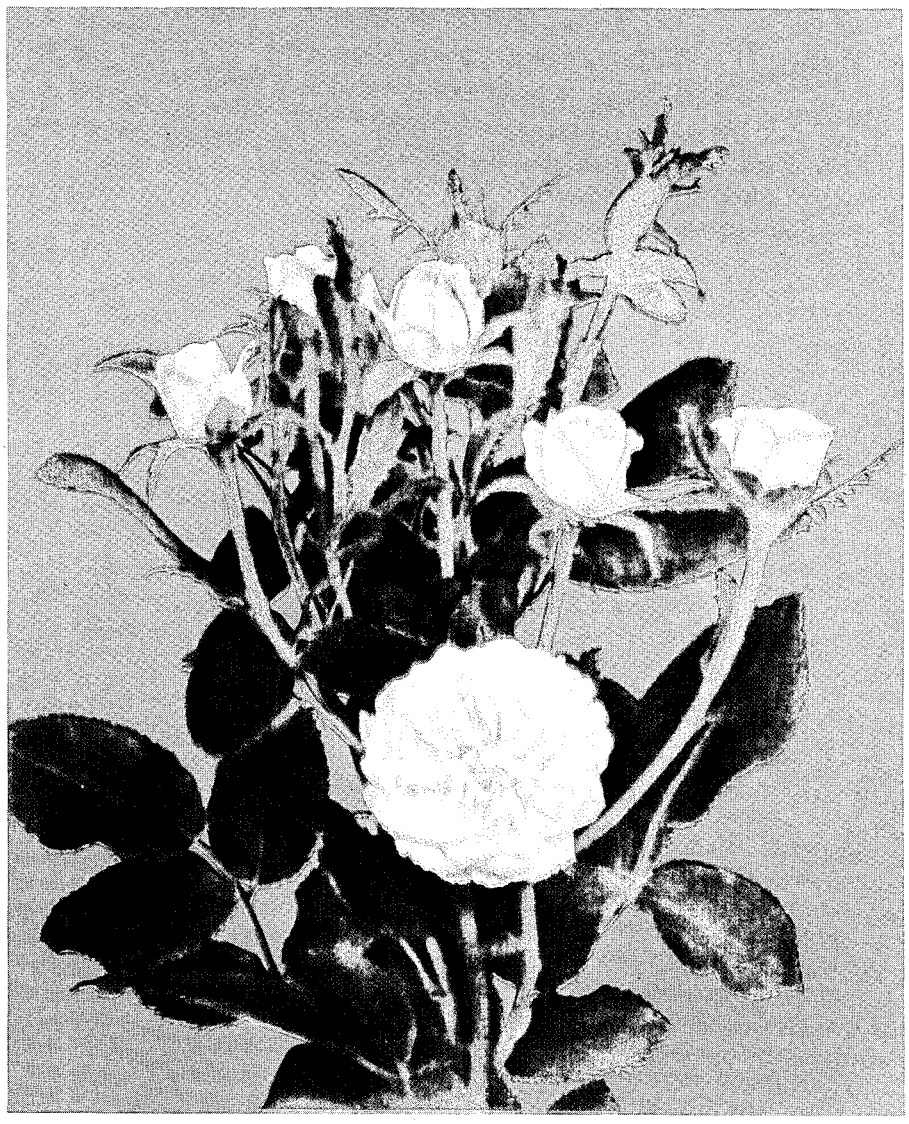
Inventor
E. S. Boerner
By Robb & Robb
Attorneys.

Patented Jan. 24, 1950 Plant Pat. 913

UNITED STATES PATENT OFFICE

913

ROSE PLANT

Eugene S. Boerner, Newark, N. Y., assignor to Jackson & Perkins Company, Newark, N. Y., a corporation of New York Application December 2, 1948, Serial No. 63,154

1 Claim. (Cl. 47—61)

The present invention relates to a new and distinct variety of rose plant of the Floribunda class, originating as a sport of the variety "Garnette."

This new variety is noted for its new combination of characteristics, distinguishing it from its parent and other known roses of its class. These dominating distinctions may be listed as follows:

(1) Tinted Rose Pink color of its blossoms, giving it a very live appearance, these blossoms having only a minimum of blue or violet cast.

(2) Long lasting quality of the blossoms, notably retaining their shape and color for as much as ten days to two weeks.

(3) Double serrated miniature holly-like foliage with long ovoid leaflets.

(4) Leathery texture and color of the leaves.

(5) Freedom of bloom and bushy habit of growth of the plant.

Asexual reproduction of this new variety shows the foregoing characteristics come true to form and are established.

In the accompanying drawing are shown specimens of the plant foliage and blossoms at different stages of development.

The following is a detailed description of the new variety, color terminology being in accordance with Ridgway's Color Standards and Nomenclature:

Parentage: Sport.

*Parent.*—"Garnette" (unpatented).

Classification: Botanic—Large flowered polyantha. Commercial—Floribunda.

*Flower*

(Observations made in the greenhouse of Jackson & Perkins Company, Newark, New York, in the morning in the month of November.)

Blooming habit: Recurrent—continuous.

Bud:

*Size.*—Small.

*Form.*—Ovoid. Is not affected by wet or hot weather.

*Color.*—When sepals first divide—Spinel Red, Plate 26; when petals begin to unfurl—Thulite Pink, Plate 26; when half blown—inside of petals—Deep Rose Pink, Plate 12; reverse of petals—Thulite Pink, Plate 26.

*Sepals.*—Branched. Curl back when petals begin to unfurl. *Color*—inside—Pale Veronese Green, Plate 18; outside—Light Cress Green, Plate 31.

*Calyx.*—Shape—funnel. Size—small. Aspect—Smooth. Odor when rubbed—none. Color—Light Cress Green, Plate. 31.

*Peduncle.*—Length—long. Aspect—Prickly. Color—Courge Green, Plate 17. Strength—erect; slender.

*Opening.*—Bud opens up well. Is not affected by adverse weather conditions.

Bloom:

*Size.*—Small. Average size when fully expanded, 2 inches.

*Borne.*—Singly and in clusters of irregular arrangement.

*Stems.*—Medium length; strong.

*Form.*—When first open—cupped. Permanence—flattens.

*Petalage.*—Very double (many petals and stamens hidden). Number of petals under normal conditions, 52.

*Color.*—Center of flower—Deep Rose Pink, Plate 12. Outer petals—Thulite Pink, Plate 26. Base of petals (aiglet)—Pale Chalcedony Yellow, Plate 17. Inside of petals—Rose Pink, Plate 12, tinted with Rose Red, Plate 12. Reverse of petals—Rose Pink, Plate 12. General tonality from a distance—Rose Pink, Plate 12; shadows deepened to Rose Color, Plate 12.

*Discoloration.*—General tonality at end of first day—Rose Pink, Plate 12; shadows deepened to Rose Color, Plate 12. Second day—Rose Pink, Plate 12; shadows deepened to Rose Color, Plate 12. Third day—Rose Pink, Plate 12; shadows deepened to Rose Color, Plate 12.

Petals:

*Texture.*—Thick. Is not affected by wet or hot weather.

*Appearance.*—Inside—velvety; outside—satiny.

*Form.*—Oval.

*Arrangement.*—Imbricated (regularly arranged shingle-like). Petaloids in center—none.

*Persistence.*—Drop off cleanly after a long period.

*Fragrance.*—Moderate. Nature—"Old Rose perfume" (Centifolia).

*Lasting quality.*—On the plant and as cut flower—very long.

Genital organs:

*Stamens, anthers.*—Small; many. Color—Naples Yellow, Plate 16. Arrangement—regular around styles.

*Stamens, filaments (threads).*—Medium length. Color—Light Buff, Plate 15.
*Pollen.*—Color—Cream Color, Plate 16.
*Styles.*—Bunched even; medium length; thin.
*Stigmas.*—Color—Barium Yellow, Plate 16.
*Ovaries.*—All enclosed in calyx.

*Plant*

Form: Bush.
Growth: Vigorous; branching.
Foliage: 3, 5 and 7 leaflets.
*Size.*—Medium.
*Quantity.*—Abundant.
*Color.*—New foliage: upper side—Hay's Russet, Plate 14; under side—Tawny, Plate 15. Old foliage: upper side—Varley's Green, Plate 18; under side—Hellebore Green, Plate 17.
*Shape.*—Long oval pointed.
*Texture.*—Upper side—leathery, corrugated; under side—smooth. Ribs and veins—prominent.
*Edge.*—Serrated (saw toothed), undulated.
*Serration.*—Double; small; sharp.
*Leaf stem.*—Color—Light Hellebore Green, Plate 17. Under side—Prickles.
*Stipules.*—Short; bearded.
*Disease resistance.*—Resistant.

Wood:
*New wood.*—Color—Wood Brown, Plate 40. Bark—Smooth.
*Old wood.*—Color—Cress Green, Plate 31. Bark—smooth.
Thorns:
*Thorns.*—On main stalks from base—ordinary. On laterals from stalk—ordinary. Form—broad base; long; slightly hooked downward. Color when young—Fawn Color, Plate 40. Position—irregular.
*Prickles.*—On main stalks—few; on laterals—none. Color—Rainette Green, Plate 31.
*Short needles.*—On main stalks and on laterals—none.

I claim:

A new and distinct variety of rose plant of the polyantha class, characterized as to novelty by the live pink color of the blossoms, their long lasting quality while retaining both shape and color, double-serrated holly-like foliage with long ovoid leaflets, leathery texture and color of the foliage, bushy habit of growth of the plant and its freedom of bloom, substantially as shown and described.

EUGENE S. BOERNER.

No references cited.